United States Patent [19]

Markham

[11] Patent Number: 4,679,554

[45] Date of Patent: Jul. 14, 1987

[54] ATHLETIC SUPPORTER

[76] Inventor: Daniel S. Markham, 124 Irving St., Laurel, Md. 20707

[21] Appl. No.: 726,159

[22] Filed: Apr. 23, 1985

[51] Int. Cl.$^4$ ............................................. A61F 5/40
[52] U.S. Cl. ..................................................... 128/158
[58] Field of Search ................................ 128/158, 160

[56] References Cited

U.S. PATENT DOCUMENTS

| Re. 23,334 | 1/1951 | Montmarquet | 128/158 |
|---|---|---|---|
| 436,518 | 9/1890 | Dent | 128/158 |
| 2,454,507 | 11/1948 | Flaherty | 128/158 |
| 4,134,400 | 1/1979 | Di Matteo | 128/158 |
| 4,590,931 | 5/1986 | Kidwell, Jr. | 128/158 |

Primary Examiner—Gregory E. McNeill

Attorney, Agent, or Firm—Hopgood, Calimafde, Kalil, Blaustein & Judlowe

[57] ABSTRACT

An athletic supporter is provided having in combination as elements of construction a waistband, leg straps and a genital-supporting pouch. At least the waistband and the pouch of the supporter consist essentially of a knitted or woven fabric of elasticized polypropylene fiber which in the form of a fabric has a coefficient of stretch in all directions of at least about 50% per linear inch and a recovery to the unstretched state in excess of about 95%. The polypropylene fabric, which preferably contains spandex, is characterized by a substantial degree of moisture transfer, with the fibers thereof substantially non-absorbent to moisture, the polypropylene fiber having a specific gravity of approximately 0.9.

15 Claims, 15 Drawing Figures

ATHLETIC SUPPORTER

This invention relates to an athletic supporter and, in particular, to an athletic supporter formed of elasticized polypropylene fabric.

STATE OF THE ART

Athletic supporters are known made of elasticized fabric, such as cotton webbing elasticized with rubber strands. In U.S. Pat. No. 2,454,507, an athletic supporter is disclosed comprising a waistband made of elastic knitted webbing in which a plurality of rubber strands are used extending lengthwise at spaced intervals in the webbing. The pouch attached to the waistband is also made of elastic knitted material, as are the understraps (leg strap means).

A disadvantage of the aforementioned supporter is that cotton is water absorbent and retains moisture because of its inferior moisture transfer property. Thus, prolonged use generally leads to discomfort to the wearer. Moreover, rubber strands tend to lose elasticity with time as evidenced by a generally stretching or creep of the supporter as well as general deterioration of cotton or other material fibers.

An athletic supporter is disclosed in U.S. Pat. No. 3,504,671 comprising a waistband made of a wide longitudinal strip of elastic fabric and a pouch capable of stretching longitudinally and transversely so as to provide a two-way stretch when worn in the region of the crotch. The ends of the longitudinally extensible fabric are secured together to form a belt or waistband. The pouch, according to FIG. 1 of the patent, has a transversely extending top edge portion secured to a pair of longitudinally extensible fabric bands, the upper ends of which are secured to the belt at locations spaced longitudinally of the belt, the pair of bands extending obliquely downwardly from the belt to the pouch in converging relationship and secured at the lower ends thereof to the pouch. The belt portion to which the bands are secured together with the obliquely extending bands form a triangular extensible structure having longitudinally extensible legs. Leg strap means are connected to the belt which extend and are secured to the lower end of the pouch. The legs of the triangular structure provide two functions: (1) they exert upward and inward pressure on the abdominal wall, and (2) they provide an uplifting support for the genitals.

A disadvantage of this design is that the wide belt is only extensible lengthwise, but not crosswise. Thus, when the wearer of the support bends his body, the belt does not extend or stretch crosswise thereby slipping at the hip region of the body and thereby cause rashes to form about the hip region. Moreover, the triangular structure is produced by lap-seaming with the edges of the lap-seam directly in contact with the skin which can create discomfort.

In addition, such athletic supporters are generally made of cotton which absorb and retain moisture which over a prolonged period of wearing time result in discomfort to the wearer.

Other types of athletic supporters are disclosed in U.S. Pat. Nos. 3,547,117, 4,186,739, and 4,453,541.

It would be desirable to provide an athletic supporter made of a fabric produced from a synthetic fiber in which the fabric is characterized by substantially efficient moisture transfer, which does not absorb and retain moisture as is characteristic of cotton, which is intrinsically luxuriously soft, which is elastically capable of stretching in all directions while exhibiting substantially complete elastic recovery, and in which the supporter is preferably constructed so as to minimize chafing of sensitive skin, while being strong and durable enough to resist coming apart due to excess physical activity and successive washings.

OBJECTS OF THE INVENTION

It is thus an object of the invention to provide an athletic supporter of synthetic material which is capable of stretching substantially in all directions, which is characterized by improved moisture transfer, and in which the fibers thereof are substantially non-absorbent to moisture.

Another object of the invention is directed to a method for producing the athletic supporter.

These and other objects will more clearly appear when taken in conjunction with the following drawings, the specification and the appended claims, wherein:

SUMMARY OF THE INVENTION

Figure 1:
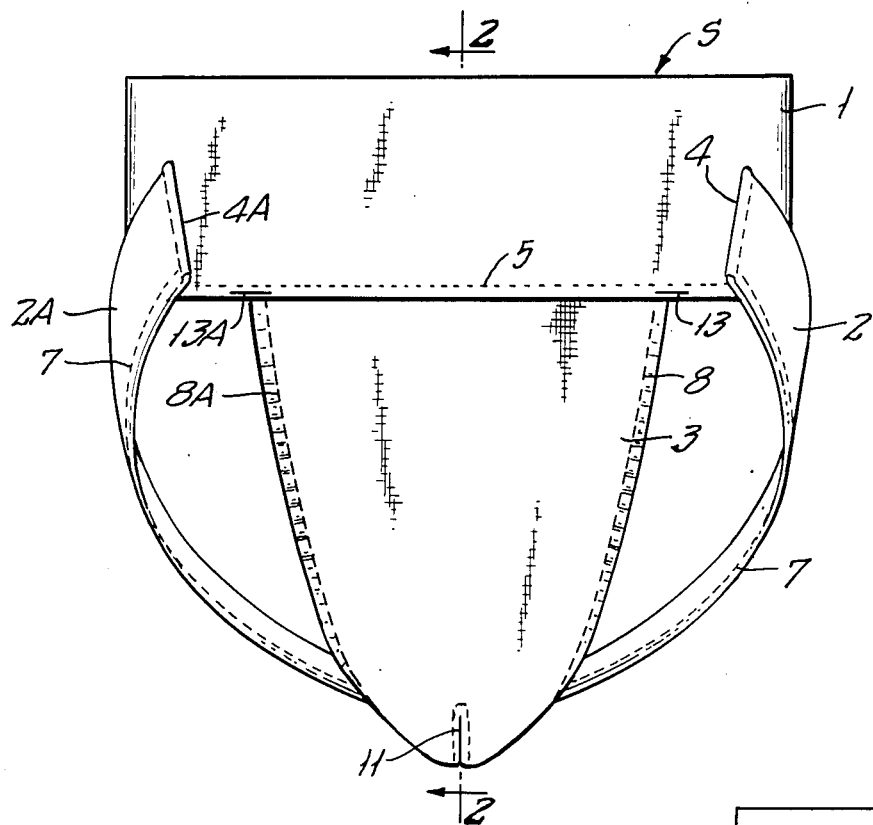
FIG. 1 is illustrative of one embodiment of the athletic supporter of the invention showing the various elements making up the support, the waistband being made of a flat tube of fabric.

Stating it broadly, the invention is directed to an athletic supporter comprising in combination as elements of construction a waistband, leg straps and a genital-supporting pouch, but in which at least the waistband and the pouch consist essentially of a knitted or woven fabric of elasticized polypropylene fiber which in the form of a fabric has a coefficient of stretch in all directions of at least about 50% per linear inch and a recovery to the unstretched state in excess of about 95%, the polypropylene fabric being characterized by a substantial degree of moisture transfer with the fibers thereof substantially non-absorbent to moisture, the polypropylene fiber having a specific gravity of approximately 0.9.

Polypropylene fabric is preferred because of its properties. It is particularly lightweight. Polypropylene fiber has a density of approximately 0.9 compared to 1.14 for nylon and 1.55 for cotton. It is substantially non-absorbent to moisture, e.g., perspiration; whereas, cotton has a high degree of water absorption. In addition, polypropylene fabric has a high degree of moisture transfer through capillary openings of the weave and is, therefore, quick drying. Its moisture regain is generally in the neighborhood of about zero %.

Polypropylene is an olefin fiber which in the form of a fabric dries quickly and requires little or no ironing. At up to 5% elongation, the fibers have an elastic recovery of 100%; at 10% elongation, it has a recovery of 95 to 100% and at 15% elongation, the fibers recover more than 90%. However, when combined with spandex in the form of a fabric, the coefficient of stretch, as stated hereinabove, is at least about 50% per linear inch and its recovery to the unstretched condition at least about 95%. A further advantage of using polypropylene is that the fibers thereof have good resistance to microorganisms, such as mildew and bacteria, and to insects such as moths, beetles, and other household pests.

Polypropylene fabric is luxuriously soft and does not chafe sensitive skin. A preferred fabric composition is one in which the polypropylene is the major fiber and the balance is spandex. A spandex material sold under the trademark "Lycra" is particularly useful. A polypropylene fabric containing over 75% by weight polypropylene, e.g., over 80%, and the balance spandex is particularly desirable. A preferred composition is approximately 82% polypropylene and 18% spandex.

The Condensed Chemical Dictionary (Eighth Edition) published by Van Nostrand Reinhold Company (1966) defines spandex at page 818 as a generic name for a synthetic fiber in which the fiber-forming substance is a long chain synthetic polymer comprised of at least 85% of a segmented polyurethane characterized by a high degree of elasticity. A typical spandex material as stated above is that known by the trademark "Lycra". The fiber is in the form of continuous monofilaments and is available in yarn with denier from 40 to 2240. Its specific gravity is about 1.21 and has a high elongation when tensile tested to the breaking point.

Polypropylene fiber is substantially stronger than spandex. It has a tensile strength of about 3 to 7 grams per denier compared to spandex which is about 0.75 to 0.9. As stated previously, its moisture regain at 65% relative humidity and 70° F.±2° F. is about zero %, whereas, cotton is 8.5 to 10.3% and nylon is 4.5%. The moisture regain at 95% relative humidity and 70° F.±2° F. (such as developed by perspiration underneath the athletic supporter) is still in the neighborhood of about zero % for polypropylene; whereas, for cotton it reaches a substantially high regain of approximately 15%, while nylon reaches a regain of about 6.5 to 8.5%. Spandex, on the other hand exhibits a relatively low moisture regain of about 0.3 to 1.3% at 65% relative humidity and only a moisture regain of about 1 to 2% at 95% relative humidity. The polypropylene/spandex fabric employed in the supporter has an elastic recovery of at least about 95% to the unstretched state. Its moisture regain at about 65% relative humidity is less than about 2%, and generally less than about 1% and down to about zero %.

By combining spandex with polypropylene fiber a unique fabric is provided for use in the construction of athletic supporters, the fabric itself being characterized by a high degree of moisture transfer through the capillaries of the knit or weave.

In a preferred embodiment, the invention is directed to an athletic supporter comprising in combination a waistband, leg strap means and a genital-supporting pouch, the supporter consisting essentially of a knitted or woven fabric of elasticized polypropylene fiber, the fabric having a coefficient of stretch in all directions of at least about 50% per linear inch and an elastic recovery in the unstretched state of at least about 95%.

The waistband is formed of a flat tube of the fabric produced from a waistband blank folded longitudinally upon itself and sewn together along superposed longitudinal edges and turned inside out to form a hidden tucked-in seam, the pouch having a top edge disposed between and anchored by the tucked-in seam, with side edges of the pouch depending downwardly therefrom and tapering into a substantially smooth round terminal portion to thereby provide a crotch-fitting shape thereof.

Leg strap means is provided formed of a flat tube of polypropylene fabric with the ends thereof sewn substantially to opposite sides of said waistband and to the terminal portion of the pouch, the pouch being located substantially symmetrical relative to the sewn ends, whereby a snugly fitting athletic supporter is provided of the polypropylene fabric characterized by improved moisture transfer therethrough, the fibers thereof being substantially non-absorbent to moisture.

The preferred embodiment described hereinabove is advantageous in that by employing a flat tube of the polypropylene fabric for the waistband, it is possible to sew the pouch to the waistband using a hidden tucked-in seam such that the ultimate structure at the seam portion is smooth, comfortable to the skin and strong.

One method for producing such a structure is set forth as follows, the method comprising providing a knitted or woven fabric of polypropylene-spandex material, the fabric material being characterized by a coefficient of stretch in all directions of at least about 50% per linear inch and having an elastic recovery to the unstretched state of at least about 95%. The method includes the steps of forming as elements of construction a wide elongated waistband blank having substantially parallel longitudinal edges from said fabric, and a crotch-fitting pouch blank, the pouch blank having an upper substantially horizontal edge and sides depending transversely therefrom which taper downwardly into a substantially smooth rounded edge portion to provide a crotch-fitting shape thereof.

The structure is formed by superposing the pouch blank on and across the width of the waistband blank with its horizontal edge substantially even with a longitudinal edge of said waistband blank, the pouch blank being rolled or gathered upon itself transverse to the waistband blank to fit within the width thereof while maintaining the horizontal edge substantially even with the longitudinal edge of said waistband blank. The waistband blank is folded longitudinally upon itself to form a flat tube thereof with the horizontal edge of the rolled or gathered pouch blank held between the superposed longitudinal edges of the waistband blank, all of the superposed edges then sewn together. The flat tube is then turned inside out with the sewn longitudinal edges tucked in to thereby provide a smooth waistband element with the pouch freely depending from the tucked-in edges thereof, the band element having two unconnected transverse edges at opposite ends thereof. The transverse edges are sewn together to form a continuous waistband, followed by sewing leg strap means of elastic fabric material substantially symmetrical to opposite sides of the waistband, and to the terminal portion of said pouch, such that a snugly crotch-fitting athletic supporter is provided of polypropylene fabric characterized by efficient moisture transfer properties and further characterized by being substantially nonabsorbent to moisture, while being luxuriously soft as to inhibit chafing.

DETAILS OF THE INVENTION

Figure 2:
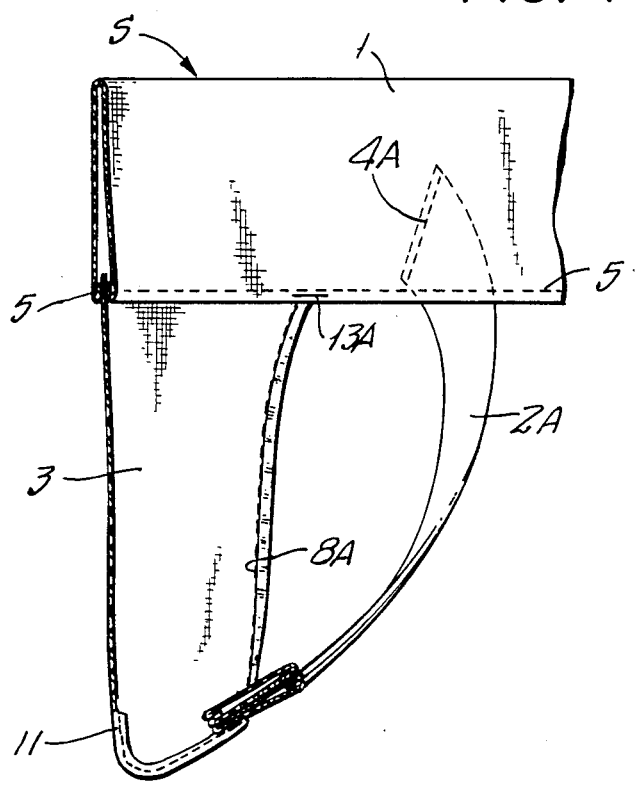
FIG. 2 is a cross section of the athletic supporter taken along line 2—2 of FIG. 1 showing the pouch sewn to the waistband with a tucked-in seam and also showing one of the leg straps.

Referring to FIG. 1 and FIG. 2, which is a side view taken along line 2—2 of FIG. 1, an athletic support S is shown comprising a waistband 1 having leg strap means with strap portions 2, 2A stitched to the waistband at 4 and 4A, respectively, the waistband having depending downwardly therefrom a pouch 3. The waistband is formed from a flat tube of polypropylene fabric, for example, a fabric comprised of 82% polypropylene and 18% spandex sold under the trademark Synera.

Figure 3:
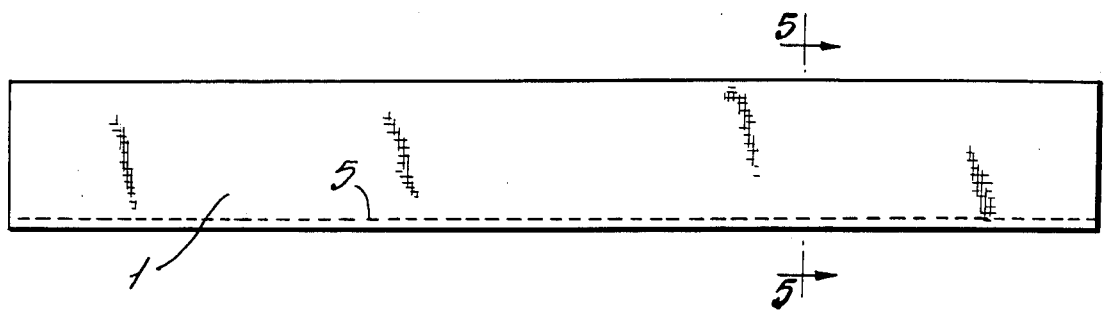
FIG. 3 depicts the waistband in the form of a flat tube prior to sewing the opposite ends together as shown in the fragment of FIG. 4.
Figure 4:
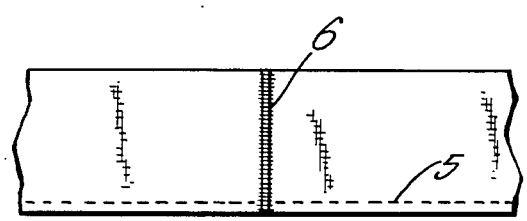
FIG. 4 is a fragment of the waistband showing the opposite ends of the waistband stitched together.
Figure 5:
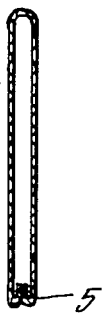
FIG. 5 is a cross section of the waistband of FIG. 3 taken along line 5—5 showing the use of a tucked-in seam in producing the waistband as a flat tube.

The flat tube is sewn on the inside via stitch 5 in the form of a hidden tucked-in seam 5 as shown in FIG. 2. This is achieved by forming the waistband as a flat tube from a folded waistband blank and sewn on the outside and then turned inside out as shown in FIG. 3 to provide hidden seam 5, also shown in FIG. 5 which is a section of FIG. 3 taken along line 5—5. The two ends of the waistband are stitched together at 6 as depicted in FIG. 4.

Figure 2A:
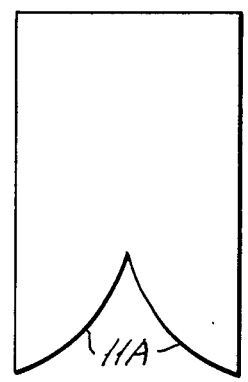
FIGS. 2A and 2B are fabric blanks for preparing the pouch, the blank of FIG. 2A having an inverted "V" cut-out with sides which are sewn together to form the pouch of FIG. 2B.
Figure 2B:
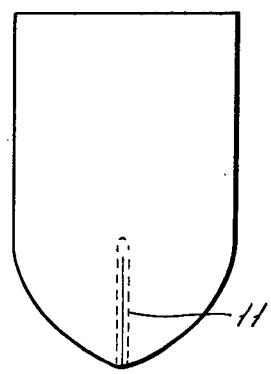
Figure 7:
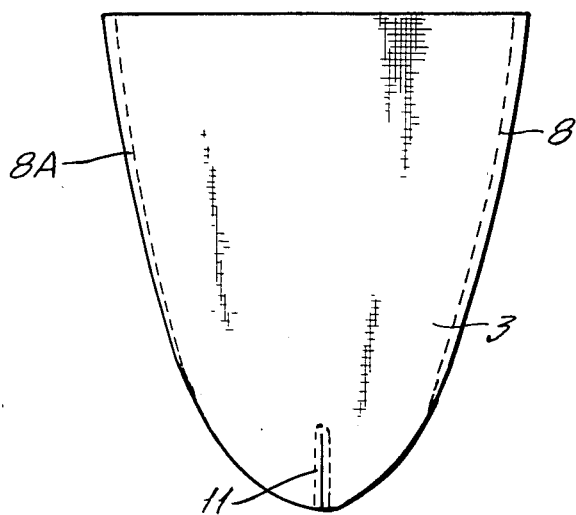
FIGS. 7 and 7A depict the pouch prior to sewing it to the waistband.
Figure 7A:
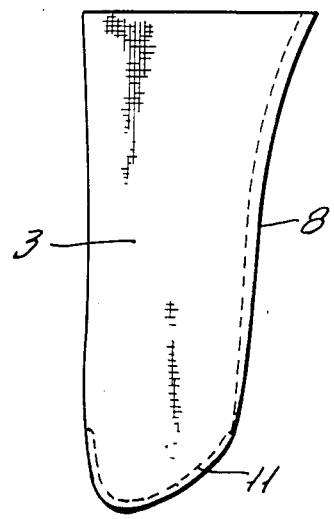

Referring back to FIGS. 1 and 2, the pouch 3 is shown stitched at 8 and 8A using an elastic element on each side of the pouch, the element being encased inside the outer side edges of the pouch. The bottom of the pouch is severed and an inverted "V" cut-out removed and the sides of the "V" sewn together or stitched at 11 (FIG. 2). This is shown in more detail in FIGS. 2A and 2B, FIG. 2A showing the pouch with the inverted "V" cut-out 11A and FIG. 2B showing the sides of the cut-out sewn together at 11 to provide a pouch with a shallow cup-like configuration. The front and side views of the pouch are shown in FIGS. 7 and 7A.

In FIGS. 1 and 2, each corner of the upper edge of the pouch is tacked by stitching at 13 and 13A, the tacks further anchoring the pouch to the waistband at the corners where stress due to stretching is higher.

Figure 8:
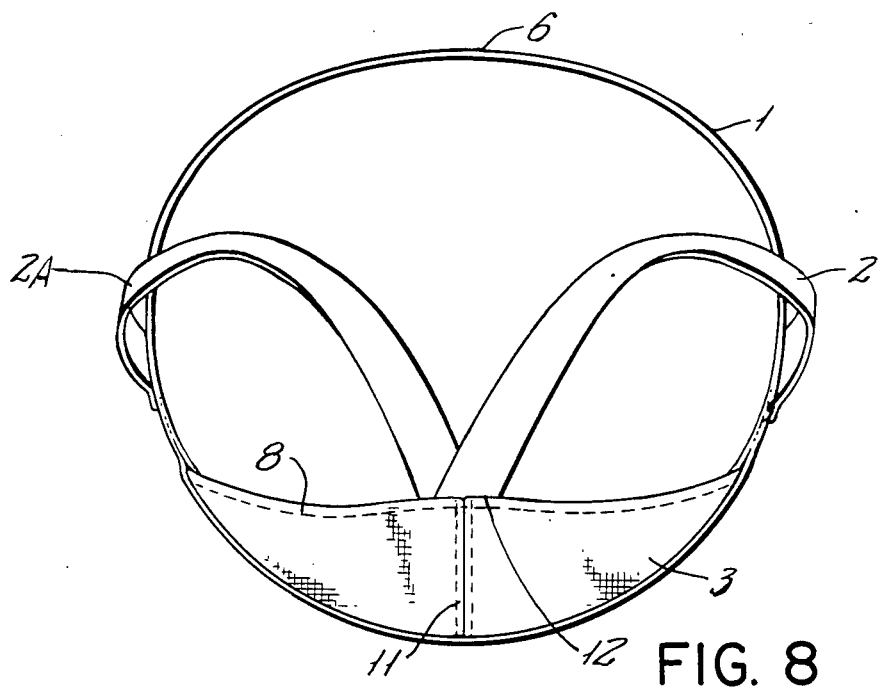
FIG. 8 is a plan view of the supporter showing the waistband spread out in the form of a circle to illustrate the attached positions of the leg strap means and the pouch relative to the waistband.

The strap means is preferably formed of a flat tube of polypropylene fabric, the flat tube being sewn with a hidden tucked-in seam 7 (FIG. 1). The strap means may comprise a single tubular strip, with the midpoint thereof sewn to the bottom of the pouch as shown in FIGS. 1 and 2, and the ends sewn to the waistband at 4 and 4A. The complete construction is shown in the plan view of FIG. 8 as viewed from above the supporter, the ends of the waistband being sewn together at 6 as previously described, the leg strap means being secured to the waistband at 2 and 2A, with the midpoint thereof secured to the pouch at 12 as shown.

Figure 6:
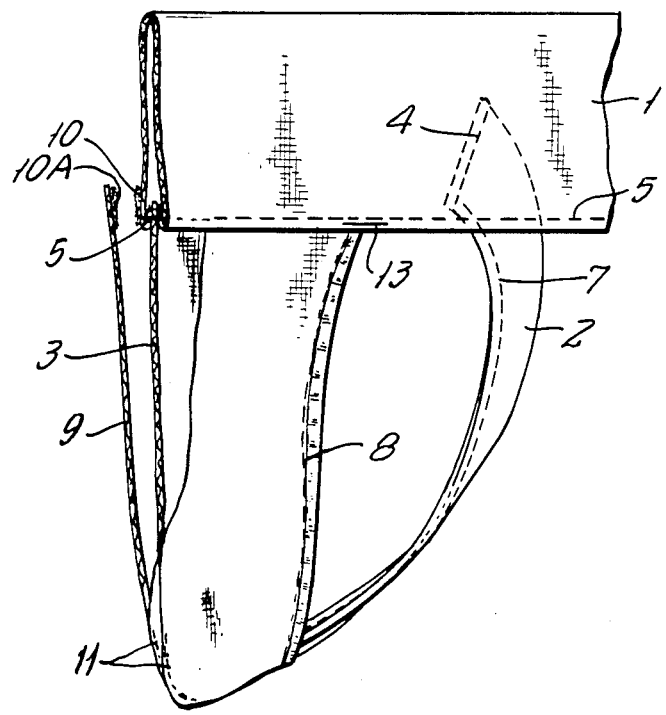
FIG. 6 is a partial cross section like FIG. 2 but showing a double-layered pouch constructed for receiving and supporting a protective cup designed to fit into the crotch.

FIG. 6 is a cross section in side view of another embodiment of the supporter showing a two layer pouch comprising outer pouch layer 9 spaced from inner pouch layer 3 and secured to 3 at 8, the upper edge of the outer pouch being securable to the front of the waistband using Velcro means 10 comprising a male patch in the form of a plastic base having a multitude of integral minute hooks which penetrate the fabric side of female patch 10A. The space is occupied by a protective cup.

Figure 9:
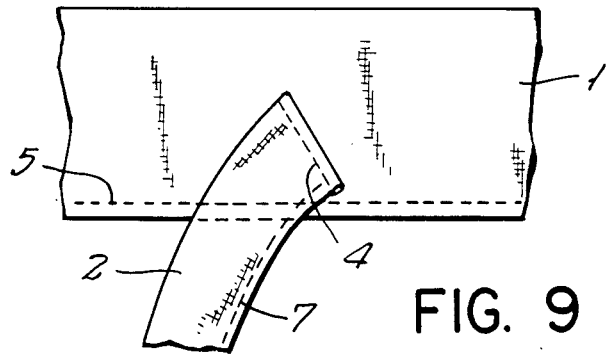
FIGS. 9 to 11 are illustrative of the several ways of connecting the leg strap means to the waistband, FIG. 11 being a cross section taken along line 11—11 of FIG. 10.
Figure 10:
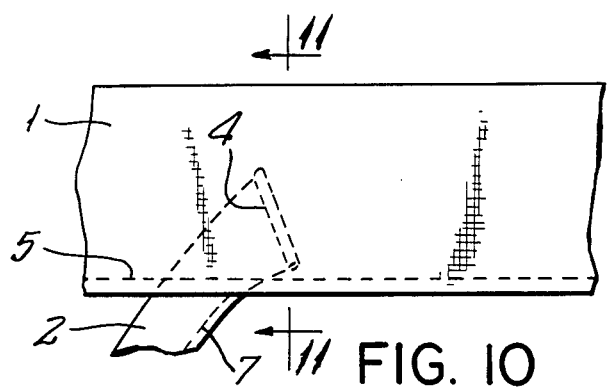
Figure 11:
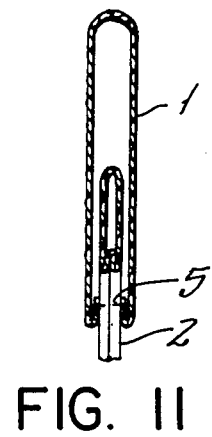

The leg strap means may be secured to the waist on either the outside or inside where the waistband is made of a flat tube fabric. FIG. 9 is a fragment of waistband 1 with leg strap 2 sewn to it at the outside thereof as an exposed seam 4. FIG. 10, on the other hand, depicts the embodiment where leg strap 2 is sewed within the flat tube which when turned inside out results in a hidden seam shown in the cross section of FIG. 11 taken along the line 11—11 of FIG. 10.

One method for producing the athletic supporter in which the pouch is sewn to the waistband using a hidden tucked-in seam is illustrated step-wise by FIGS. 12 to 15.

Figure 12:
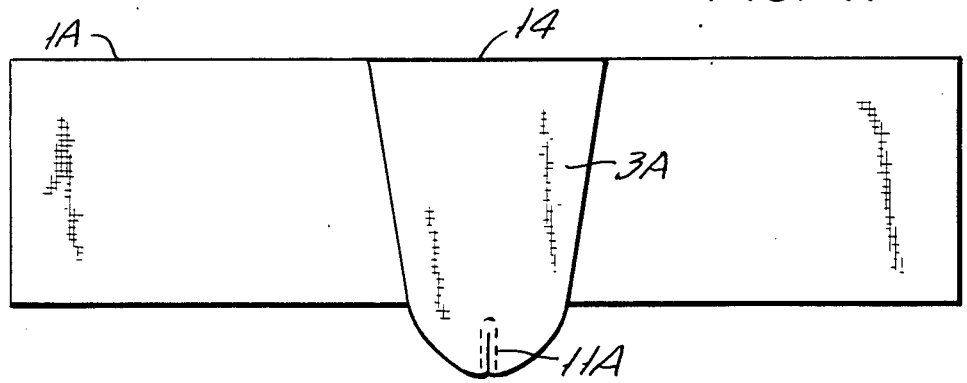
FIGS. 12 to 15 are representative of steps which may be employed in attaching a pouch to the waistband using a tucked-in seaming technique, the leg strap means being similarly attached, if desired.

Referring to FIG. 12, a waistband blank 1A is shown with a pouch blank 3A superposed on the top thereof with its upper edge 14 placed even with the upper longitudinal edge of waistband blank 1A, the pouch 3A having been previously cut with an inverted "V" at its bottom end and sewn along stitch line 11A to provide a shallow cup thereof.

Figure 13:
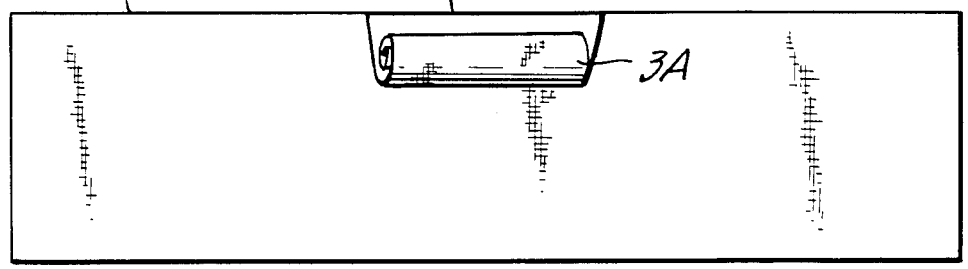
Figure 14:
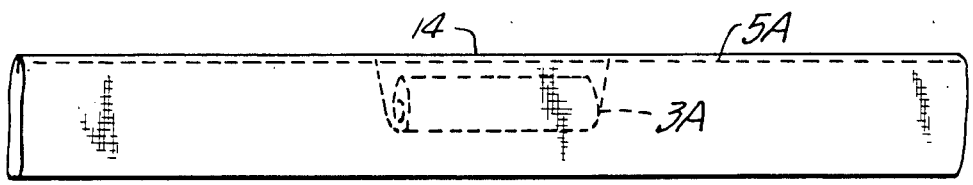

The pouch is rolled up as shown in FIG. 13 while maintaining top edge 14 even with the top longitudinal edge of the waistband blank. The blank is folded to provide a flat tube as shown in FIG. 14 with the rolled pouch within it and the assembly sewn together along stitch line 5A, with top edge 14 of the pouch sewn between the two longitudinal edges of the waistband.

Figure 15:
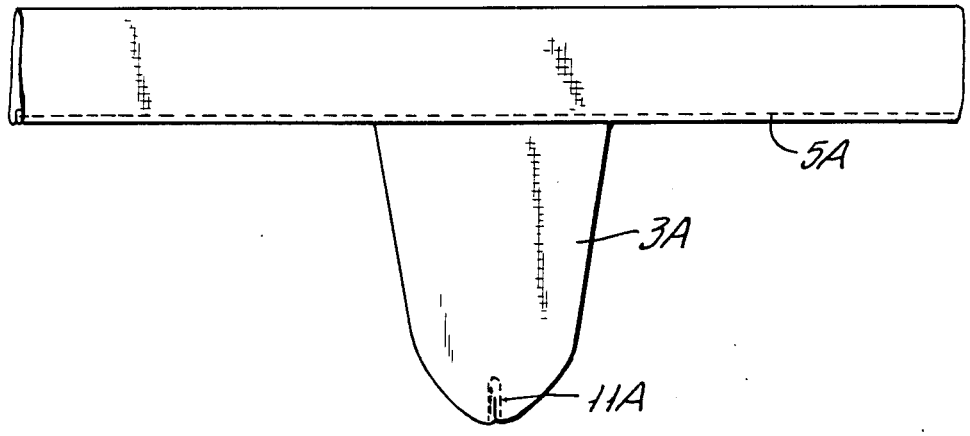

The tubular waist band is then turned inside out as shown in FIG. 15 to provide a tucked-in hidden seam 5A corresponding to seam 5 shown in the cross section of FIG. 2.

The invention is also applicable for use in athletic supporter briefs, the brief comprising in combination a waistband, a genital-supporting pouch, and support means in the form of a seat panel connected to the pouch for maintaining the pouch snugly crotch-fitting, the support means preferably covering the buttocks. The brief consists essentially of a knitted or woven fabric of elasticized polypropylene fiber, said elasticized fabric comprising a knit or weave of polypropylene fiber and spandex fiber, with the polypropylene fiber constituting the major portion of the fabric, the fabric having a coefficient of stretch in all directions of at least about 50% per linear inch and an elastic recovery in the unstretched state of at least about 95%.

The waistband is formed of a flat tube of the fabric produced from a waistband blank folded longitudinally upon itself and sewn together along superposed longitudinal edges with the edges tucked in to form a hidden tucked-in seam, the pouch having a top edge disposed between and anchored by the tucked-in seam, with side edges of the pouch depending downwardly therefrom and tapering into a substantially smooth terminal portion to thereby provide a crotch-fitting shape thereof.

The support means is formed of said polypropylene fabric and in one embodiment provides a seat panel which is sewn to the waistband with a hidden tucked-in seam and which extends and is sewn to the terminal portion of the pouch. Thus, a snugly fitting athletic supporter brief is provided characterized by a substantial degree of moisture transfer therethrough, the fibers thereof being substantially non-absorbent to moisture, the brief being further characterized by minimum skin chafing when worn.

Although the present invention has been described in conjunction with the preferred embodiments, it is to be understood that modifications and variations may be resorted to without departing from the spirit and scope of the invention as those skilled in the art will readily understand. Such modifications and variations are considered to be within the purview and scope of the invention and the appended claims.

What is claimed is:

1. In an athletic supporter having in combination as elements of construction a waistband, leg straps and a genital-supporting pouch, the improvement,
wherein at least the waistband and the pouch consist essentially of a knitted or woven fabric of elasticized polypropylene fiber formed of polypropylene and spandex fibers with the polypropylene fiber constituting the major portion of the fabric, said fabric having a coefficient of stretch in all directions of at least 50% per linear inch and a recovery to the unstretched state in excess of about 95%,
said polypropylene fabric being characterized by a substantial degree of moisture transfer, with the fibers thereof substantially non-absorbant to moisture,
said polypropylene fiber having a specific gravity of approximately 0.9.

2. The athletic supporter of claim 1, wherein the fabric comprises approximately 82% polypropylene fiber and approximately 18% spandex fiber.

3. An athletic supporter comprising in combination a waistband, leg strap means and a genital-supporting pouch,
said supporter consisting essentially of a knitted or woven fabric of elasticized polypropylene fiber formed of polypropylene and spandex fibers, with the polypropylene fiber constituting the major portion of the fabric, said fabric having a coefficient of stretch in all directions of at least about 50% per linear inch and an elastic recovery in the unstretched state of at least about 95%,
said waistband being formed of a flat tube of the fabric produced from the waistband blank folded longitudinally upon itself and sewn together along superposed longitudinal edges with the edges tucked in to form a hidden tucked-in seam,
said pouch having a top edge disposed between and anchored by the tucked-in seam, with side edges of the pouch depending downwardly therefrom and tapering into a substantially smooth terminal portion to thereby provide a crotch-fitting shape thereof,
and leg strap means formed of a flat tube of polypropylene fabric with the ends thereof sewn substantially to opposite side of said waistband and to the terminal portion of the pouch, the pouch being located substantially symmetrical relative to the sewn ends,
whereby a snugly fitting athletic supporter is provided of said polypropylene fabric characterized by a substantial degree of moisture transfer therethrough, the fibers thereof being substantially non-absorbant to moisture.

4. The athletic supporter of claim 4, wherein the fabric consists essentially of approximately 82% polypropylene fiber and approximately 18% spandex fiber.

5. The athletic supporter of claim 4, wherein the leg strap means is sewn to the waistband with a hidden tucked-in seam.

6. An athletic supporter comprising in combination a waistband, leg strap means and a genital-supporting pouch,
said supporter consisting essentially of a knitted or woven fabric of elasticized polypropylene fiber, said elasticized fabric comprising a knit or weave of polypropylene fiber and spandex fiber, with the polypropylene fiber constituting the major portion of the fabric, said fabric having a coefficient of stretch in all directions of at least about 50% per linear inch and an elastic recovery in the unstretched state of at least about 95%,
said waistband being formed of a flat tube of the fabric produced from a waistband blank folded longitudinally upon itself and sewn together along superposed longitudinal edges with the edges tucked in to form a hidden tucked-in seam,
said pouch having a top edge disposed between and anchored by the tucked-in seam, with side edges of the pouch depending downwardly therefrom and tapering into a substantially smooth terminal portion to thereby provide a crotch-fitting shape thereof,
and leg strap means formed of a flat tube of polypropylene fabric with the ends thereof sewn substantially to opposite sides of said waistband with a hidden tucked-in seam and to the terminal portion of the pouch, the pouch being located substantially symmetrical relative to the sewn ends,
whereby a snugly fitting athletic supporter is provided of said polypropylene fabric characterized by a substantial degree of moisture transfer therethrough of body perspiration, the fibers thereof being substantially non-absorbant to moisture, said supporter being further characterized by minimum skin chafing when worn.

7. The athletic supporter of claim 6, wherein the fabric consists essentially of approximately 82% polypropylene fiber and approximately 18% spandex fiber.

8. A method for producing an athletic supporter which comprises,
providing a knitted or woven fabric of polypropylene-spandex material of which a major portion is comprised of polypropylene fiber,
said fabric material being characterized by a coefficient of stretch in all directions of at least about 50% per linear inch and having an elastic recovery to the unstretched state of at least about 95%,
forming as elements of construction a wide elongated waistband blank having substantially parallel longitudinal edges from said fabric, and a crotch-fitting pouch blank,
said pouch blank having an upper substantially horizontal edge and sides depending transversely therefrom which taper downwardly into a substantially smooth edge portion to provide a crotch-fitting shape thereof,
superposing said pouch blank on and across the width of said waistband blank with its horizontal edge substantially even with a longitudinal edge of said waistband blank, said pouch blank being rolled or gathered upon itself transverse to said waistband blank to fit within the width thereof while maintaining the horizontal edge substantially even with the longitudinal edge of said waistband blank, folding said waistband blank longitudinally upon itself to form a flat tube thereof with said horizontal edge of the rolled pouch blank held between the superposed longitudinal edges of said waistband blank, sewing all of the superposed edges together, turning said flat tube inside out with the sewn longitudinal edges tucked in and thereby provide a smooth waistband element with the pouch freely depending from the tucked-in edges thereof, said band element having two unconnected transverse edges at opposite ends thereof, sewing said transverse edges together to form a continuous waistband, and sewing leg strap means of elastic fabric material symmetrical to opposite sides of the waistband, and to the terminal portion of said pouch, whereby a snugly crotch-fitting athletic supporter is provided of polypropylene fabric characterized by a substantial degree of moisture transfer and by being substantially non-absorbent to moisture.

9. The method of claim 8, wherein the polypropylene-spandex fabric consists essentially of approximately 82% polypropylene and approximately 18% spandex.

10. The method of claim 8, wherein before the waistband blank is folded over, leg strap means is sewn to the waistband blank symmetrical on each side of the sewn pouch and to the terminal portion of the pouch, such as to provide a hidden tucked-in seam between opposite ends of the leg strap means and said waistband when the flat tube of said waistband is turned inside out.

11. A method for producing an athletic supporter which comprises, providing a knitted or woven fabric of polypropylene-spandex material of which a major portion is comprised of polypropylene fiber, said fabric material being characterized by a coefficient of stretch in all directions of at least about 50% per linear inch and having an elastic recovery to the unstretched state of at least about 95%, forming as elements of construction a wide elongated waistband blank having substantially parallel longitudinal edges from said fabric, and a crotch-fitting pouch blank, said pouch blank having an upper substantially horizontal edge and sides depending transversely therefrom which taper downwardly into a substantially smooth edge portion to provide a crotch-fitting shape thereof, superposing said pouch blank on and across the width of said waistband blank with its horizontal edge substantially even with a longitudinal edge of said waistband blank, sewing ends of leg strap means to said waistband blank symmetrical to each side of said pouch and to said smooth end portion of said pouch, said pouch blank being rolled or gathered upon itself together with said leg strap means transverse to said waistband blank to fit within the width thereof while maintaining the horizontal edge substantially even with the longitudinal edge of said waistband blank, folding said waistband blank longitudinally upon itself to form a flat tube thereof with said horizontal edge of the rolled pouch blank held between the superposed longitudinal edges of said waistband blank, sewing all of the superposed edges together, turning said flat tube inside out with the sewn longitudinal edges tucked in and the sewn ends of the leg strap means also tucked in and thereby provide a smooth waistband element with the pouch freely depending from the tucked-in edges thereof, said band element having two unconnected transverse edges at opposite ends thereof, and sewing said transverse edges together to form a continuous waistband, whereby a snugly crotch-fitting athletic supporter is provided of polypropylene fabric characterized by a substantial degree of moisture transfer and by being substantially non-absorbent to moisture, said supporter being further characterized by minimum skin chafing when worn.

12. The athletic supporter of claim 11, wherein the fabric consists essentially of approximately 82% polypropylene fiber and approximately 18% spandex fiber.

13. The athletic supporter of claim 3, wherein said pouch is comprised of two separable layers of fabric which define a space therebetween for receiving and supporting a protective cup.

14. The method of claim 8, wherein the pouch thereof is formed of two separable layers of fabric which define a space therebetween for receiving and supporting a protective cup.

15. An athletic supporter brief comprising in combination a waistband, a genital-supporting pouch, and support means connected to the pouch for maintaining the pouch snugly crotch-fitting, said supporter brief consisting essentially of a knitted or woven fabric of elasticized polypropylene fiber, said elasticized fabric comprising a knit or weave of polypropylene fiber and spandex fiber, with the polypropylene fiber constituting the major portion of the fabric, said fabric having a coefficient of stretch in all directions of at least about 50% per linear inch and an elastic recovery in the unstretched state of at least about 95%, said waistband being formed of a flat tube of the fabric produced from a waistband blank folded longitudinally upon itself and sewn together along superposed longitudinal edges with the edges tucked in to form a hidden tucked-in seam, said pouch having a top edge disposed between and anchored by the tucked-in seam, with side edges of the pouch depending downwardly therefrom and tapering into a substantially smooth terminal portion to thereby provide a crotch-fitting shape thereof, and support means for maintaining said pouch snugly crotch-fitting formed of said polypropylene fabric sewn to said waistband with a hidden tucked-in seam and to the terminal portion of the pouch, whereby a snugly fitting athletic supporter brief is provided of said polypropylene fabric characterized by a substantial degree of moisture transfer therethrough, the fibers thereof being substantially non-absorbent to moisture, said brief being further characterized by minimum skin chafing when worn.

* * * * *